United States Patent
Dunn

(10) Patent No.: US 9,814,796 B2
(45) Date of Patent: Nov. 14, 2017

(54) METHODS FOR STERILIZATION AND/OR DISINFECTION

(71) Applicants: PERFORMANCE PACKAGING OF NEVADA, LLC, Las Vegas, NV (US); Joseph Dunn, Daytona Beach, FL (US)

(72) Inventor: Joseph Dunn, Daytona Beach, FL (US)

(73) Assignees: PERFORMANCE PACKAGING OF NEVADA, LLC, Las Vegas, NV (US); Joseph Dunn, Ormond Beach, FL (US)

( * ) Notice: Subject to any disclaimer, the term of this patent is extended or adjusted under 35 U.S.C. 154(b) by 0 days.

(21) Appl. No.: 15/046,246

(22) Filed: Feb. 17, 2016

(65) Prior Publication Data

US 2017/0027175 A1 Feb. 2, 2017

Related U.S. Application Data

(60) Provisional application No. 62/238,396, filed on Oct. 7, 2015, provisional application No. 62/199,371, filed on Jul. 31, 2015.

(51) Int. Cl.

| | |
|---|---|
| *A01N 47/06* | (2006.01) |
| *A61L 2/22* | (2006.01) |
| *A61L 2/18* | (2006.01) |
| *A01N 37/16* | (2006.01) |
| *A01N 59/00* | (2006.01) |
| *A61L 2/20* | (2006.01) |

(52) U.S. Cl.
CPC .............. *A61L 2/22* (2013.01); *A01N 37/16* (2013.01); *A01N 59/00* (2013.01); *A61L 2/18* (2013.01); *A61L 2/20* (2013.01)

(58) Field of Classification Search
CPC .............. A01N 47/06; A61L 2/22; A61L 2/18
See application file for complete search history.

(56) References Cited

U.S. PATENT DOCUMENTS

| | | | | |
|---|---|---|---|---|
| 6,211,237 B1 * | 4/2001 | Huss | ....................... | C02F 1/722 514/557 |
| 8,828,910 B2 | 9/2014 | Aksela et al. | | |
| 9,078,435 B2 * | 7/2015 | Dunn | ..................... | B65B 55/02 |
| 2013/0065958 A1 | 3/2013 | Dunn | | |
| 2014/0367334 A1 * | 12/2014 | Salonen | ............... | B01D 61/025 210/636 |
| 2015/0305342 A1 | 10/2015 | Burke et al. | | |
| 2015/0305343 A1 | 10/2015 | Burke et al. | | |
| 2015/0305344 A1 | 10/2015 | Burke et al. | | |
| 2015/0306266 A1 | 10/2015 | Burke et al. | | |
| 2015/0306269 A1 | 10/2015 | Bullard et al. | | |

FOREIGN PATENT DOCUMENTS

| | | |
|---|---|---|
| CA | 2252104 | 5/1999 |
| EP | 0231632 | 8/1987 |
| SU | 1172514 | 4/1985 |
| WO | WO 94/21120 | 9/1994 |
| WO | WO 00/18228 | 4/2000 |
| WO | WO 2006/093792 | 9/2006 |
| WO | WO 2012/037294 | 3/2012 |

OTHER PUBLICATIONS

Bydzovská et al., "Disinfecting properties of performic acid against bacteriophage phi X 174 as a model of small envelope—free viruses," *J. Hyg. Epidemiol. Microbiol. Immunol.*, 25(4):414-23 (1981). Abstract.

Kozarov et al., "Disinfectant effect of performic acid," *J. Hyg. Epidemiol. Microbiol. Immunol.*, 19(3):389-92 (1975). Abstract.

Search Report and Written Opinion issued in Int'l App. No. PCT/US2016/018312 (dated 2016).

Swern et al., "Peroxides. III.[2] Structure of Aliphatic Peracids in Solution and in the Solid State. An Infrared, X-Ray Diffraction and Molecular Weight Study[3]"; *J. Am. Chem. Soc.*, 77(21), 5537-5541 (1955).

Sun et al., "Kinetics of Formic Acid-autocatalyzed Preparation of Performic Acid in Aqueous Phase," *Chin.J.Chem.Eng.*, 19(6), 964-971 (2011).

Search Report and Written Opinion issued in Int'l App. No. PCT/US2016/044764 (dated 2017).

\* cited by examiner

*Primary Examiner* — Sarah Pihonak
*Assistant Examiner* — Jason A Deck
(74) *Attorney, Agent, or Firm* — Barnes & Thornburg LLP

(57) ABSTRACT

Methods for killing spores include contacting the spores with an aqueous solution containing performic acid. The contacting occurs at a temperature of less than or equal to about 35° C. for a period of time of less than or equal to about 15 seconds, and the contacting effects at least a 4 log reduction in a number of spores capable of reproduction, metabolism, and/or growth.

34 Claims, 1 Drawing Sheet

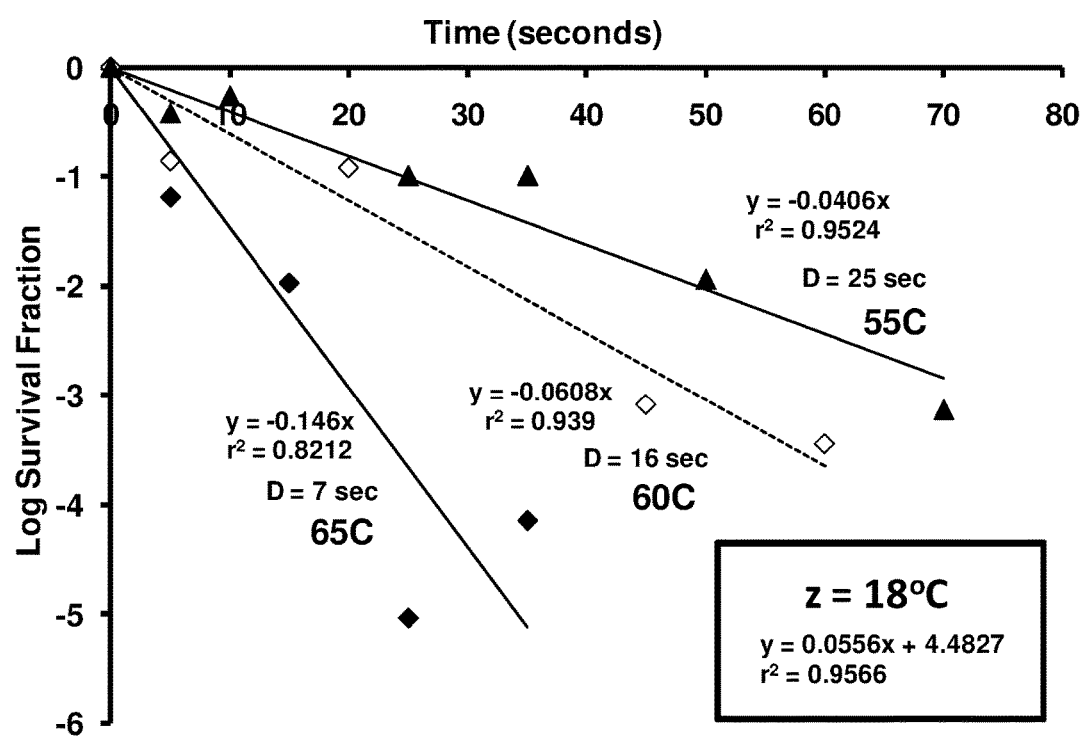

METHODS FOR STERILIZATION AND/OR DISINFECTION

RELATED APPLICATIONS

This application claims the benefit of U.S. Provisional Application No. 62/238,396, filed Oct. 7, 2015, and U.S. Provisional Application No. 62/199,371, filed Jul. 31, 2015. The entire contents of both priority documents are incorporated herein by reference, except that in the event of any inconsistent teachings or definition from the present specification, the teachings or definition herein shall be deemed to prevail.

TECHNICAL FIELD

The present teachings relate generally to methods and materials for sterilization and/or disinfection.

BACKGROUND

Disinfection and sterilization are two types of decontamination processes that are prevalent in a variety of industries, including but not limited to the food, pharmaceutical, and medical industries. Disinfection is the process of eliminating or reducing microorganisms from inanimate objects and surfaces, whereas sterilization refers to the process of killing substantially all microorganisms present in or on an environment (e.g., on a surface).

Sterilization of food, pharmaceutical, and medical packaging is used to inactivate microorganisms that may be present on the packaging. Failure to properly sterilize food and/or medical packaging may lead to contamination of the product within the package, which may lead to sickness and even death of a user of the contents thereof. Industry has developed various methods to sterilize packaging to create aseptic packaging.

Traditional aseptic packaging may be sterilized using hydrogen peroxide. As set forth in Title 37 of the Code of Federal Regulations (CFR), §178.1005, the U.S. Food and Drug Administration (FDA) has determined that a hydrogen peroxide solution containing not more than 35% hydrogen peroxide may be safely used to sterilize polymeric food-contact surfaces. However, sterilization using hydrogen peroxide typically requires high temperatures, ultraviolet light, plasma, or other agents or methods to activate the oxidative potential of the peroxide and generate hydroxyl radicals, which in turn mediate the inactivation of microorganisms on the packaging material. The temperature needed to generate free radicals from the hydrogen peroxide may be in excess of 65° C. (e.g., in the range of 120° C. to 135° C.), and hot sterile air at 85° C. is typically used to activate and blow off residuals.

Packaging to be sterilized and/or disinfected (e.g., food packaging, medical packaging, pharmaceutical packaging, etc.) may contain polymeric material. The FDA has provided a list of polymeric materials that may be utilized with hydrogen peroxide. The list, set forth in 37 CFR §178.1005 (e), includes ethylene-acrylic acid copolymers, ethylene-carbon monoxide copolymers, ethylene-methyl acrylate copolymer resins, ethylene-vinyl acetate copolymers, ionomeric resins, isobutylene polymers, olefin polymers, polycarbonate resins, polyethylene terephthalate (PET), poly-1-butene resins and butane/ethylene copolymers, polystyrene and rubber modified polystyrene polymers, and vinylidene chloride/methyl acrylate copolymers. Sterilization of some polymeric forms—including but not limited to plastic bottles—may be problematic at elevated temperatures since the polymeric materials may deform during the heating associated with the sterilization process. In addition, an extended drying process may be required to evaporate peroxide. Moreover, some plastic materials (e.g., PET) adsorb or absorb peroxide making it very difficult to achieve a residue limit of 0.5 parts per million (ppm) for food packaging as required by the FDA under 37 CFR §178.1005 (d).

An additional challenge associated with the sterilization and/or disinfection of articles carried along an automated processing line (e.g., a bottling line) is the speed with which the line is operated and the costs associated with increased processing time, distance, and/or real estate. By way of example, a modern bottling line may operate at speeds up to and possibly exceeding sixty thousand bottles per hour. Operation at such speeds places a high demand on the size, complexity, and layout of the packaging line. For example, at sixty thousand bottles-per-hour, a line filling three-inch diameter bottles and using a disinfectant/sterilant contact time of fifteen seconds would need to devote about 62.5 feet of travel distance to contact with the disinfectant/sterilization agent, not including the additional time and distance needed for application and removal of the sterilization/disinfection agent. The energy costs associated with extended sterilization/disinfection agent contact times and/or the use of heat or hot air during sterilization/disinfection and/or for removing agent residuals may be high.

SUMMARY

The scope of the present invention is defined solely by the appended claims, and is not affected to any degree by the statements within this summary.

By way of introduction, a first method for killing spores in accordance with the present teachings includes contacting the spores with an aqueous solution containing performic acid. The contacting occurs at a temperature of less than or equal to about 35° C. for a period of time of less than or equal to about 15 seconds, and the contacting effects at least a 4 log reduction in a number of spores capable of reproduction, metabolism, and/or growth.

A second method for killing spores in accordance with the present teachings includes contacting the spores with an aqueous solution containing performic acid. The contacting occurs at a temperature of less than or equal to about 30° C. for a period of time of less than or equal to about 10 seconds, and the contacting effects at least a 6 log reduction in a number of spores capable of reproduction, metabolism, and/or growth.

A third method for killing spores in accordance with the present teachings includes contacting the spores with an aqueous solution containing performic acid (and/or a mixture of formic acid and hydrogen peroxide) in an amount of at least about 1.0 weight percent based on total weight of the aqueous solution. At least a portion of the aqueous solution is in fluid communication with an aerosolized form thereof. The contacting occurs at a temperature of less than or equal to about 30° C. for a period of time of less than or equal to about 10 seconds, and the contacting effects at least a 6 log reduction in a number of spores capable of reproduction, metabolism, and/or growth.

BRIEF DESCRIPTION OF THE DRAWINGS

FIG. 1 shows a plot of the experimentally-determined response of *Bacillus atrophaeus* ATCC 9372 spores to treatment with 28% hydrogen peroxide at various temperatures.

DETAILED DESCRIPTION

Methods and materials for sterilization and/or disinfection (e.g., of a spore-containing surface) at high speed and at low temperature have been discovered and are described herein. The methods and materials described herein are active at room temperature and do not require further activation by heat, ultraviolet light, and/or the like. In some embodiments, methods and materials in accordance with the present teachings may be used for eliminating and/or reducing biological contamination present on an interior and/or an exterior surface of an article of manufacture (e.g., packaging, containers, and/or the like). In other embodiment, methods and materials in accordance with the present teachings may be used for eliminating and/or reducing biological contamination on a volume or surface of a machine (e.g., a packaging machine used for aseptic packaging). In some embodiments, methods and materials in accordance with the present teachings may be used in an automated processing line, such as for the continuous on-line sterilization/disinfection of all manner of surfaces, including but not limited to packaging, packaging materials, plastics, papers, laminates, bottles, cups, tubs, cans, seals, lids, caps, formed or pre-formed containers or structures, and/or the like. In some embodiments, methods and materials in accordance with the present teachings may also be used for the reduction or removal of chemical residuals associated with the sterilization/disinfection process.

It is to be understood that elements and features of the various representative embodiments described below may be combined in different ways to produce new embodiments that likewise fall within the scope of the present teachings.

By way of general introduction, a method for killing spores in accordance with the present teachings includes contacting the spores with an aqueous solution containing performic acid. The contacting occurs at a temperature of less than or equal to about 35° C. for a period of time of less than or equal to about 15 seconds, and the contacting effects at least a 4 log reduction in a number of spores capable of reproduction, metabolism, and/or growth.

Performic acid (PFA) is an unstable colorless liquid with strong oxidizing properties. PFA may be prepared by reacting formic acid (FA) with hydrogen peroxide as shown in EQN. (1).

EQN. (I)

The reaction shown in EQN. (1) may be catalyzed (e.g., by acid catalyst) and may be accelerated at low pH, through the addition of alcohols or esters, and/or through vigorous agitation. The source of the acid proton used for catalyzing the reaction may also derive from formic acid itself. In accordance with the present teachings, PFA may be present as an intramolecularly hydrogen-bonded monomer, as shown in formula (I), as an inter-molecularly hydrogen-bonded dimer, as shown in formula (II), or as a combination of both.

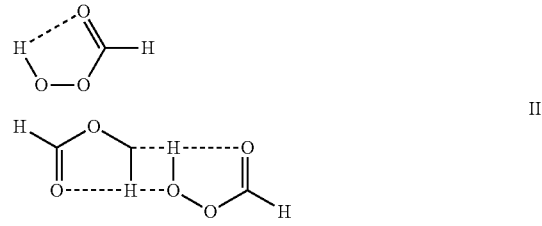

In some embodiments, methods in accordance with the present teachings further include generating the performic acid (e.g., by a reaction between a peroxide, such as hydrogen peroxide, and formic acid). In some embodiments, the PFA-containing aqueous solution further includes formic acid, hydrogen peroxide, or a combination thereof. The water present in the aqueous solution of performic acid may be distilled water, deionized water, osmosis-purified water, tap water, or a combination thereof.

The temperature at which spores are contacted with a performic-acid containing solution in accordance with the present teachings may be varied based on a particular application. In one example, the temperature is less than or equal to about 40° C. In another example, the temperature is less than or equal to about 37° C. In a further example, the temperature is less than or equal to about 36° C. In a still further example, the temperature is in a range of about 10° C. to 65° C.

The temperature at which spores are contacted with a performic-acid containing solution in accordance with the present teachings may be one of several different values or fall within one of several different ranges. For example, it is within the scope of the present teachings to select a temperature for contacting spores with a PFA-containing aqueous solution to be less than or equal to one of the following values: about 65° C., 64° C., 63° C., 62° C., 61° C., 60° C., 59° C., 58° C., 57° C., 56° C., 55° C., 54° C., 53° C., 52° C., 51° C., 50° C., 49° C., 48° C., 47° C., 46° C., 45° C., 44° C., 43° C., 42° C., 41° C., 40° C., 39° C., 38° C., 37° C., 36° C., 35° C., 34° C., 33° C., 32° C., 31° C., 30° C., 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., or 10° C.

It is also within the scope of the present teachings for the temperature at which spores are contacted with a performic-acid containing solution in accordance with the present teachings to fall within one of many different ranges. In a first set of ranges, the temperature is in one of the following ranges: 5° C. to 45° C., 5° C. to 44° C., 5° C. to 43° C., 5° C. to 42° C., 5° C. to 41° C., 5° C. to 40° C., 5° C. to 39° C., 5° C. to 38° C., 5° C. to 37° C., 5° C. to 36° C., 5° C. to 35° C., 5° C. to 34° C., 5° C. to 33° C., 5° C. to 32° C., 5° C. to 31° C., 5° C. to 30° C., 5° C. to 29° C., 5° C. to 28° C., 5° C. to 27° C., 5° C. to 26° C., 5° C. to 25° C., 5° C. to 24° C., 5° C. to 23° C., 5° C. to 22° C., 5° C. to 21° C., 5° C. to 20° C., 5° C. to 19° C., 5° C. to 18° C., 5° C. to 17° C., 5° C. to 16° C., 5° C. to 15° C., 5° C. to 14° C., 5° C. to 13° C., 5° C. to 12° C., 5° C. to 11° C., and 5° C. to 10° C. In a second set of ranges, the temperature is in one of the following ranges: 6° C. to 39° C., 7° C. to 39° C., 8° C. to 39° C., 9° C. to 39° C., 10° C. to 39° C., 11° C. to 39° C., 12° C. to 39° C., 13° C. to 39° C., 14° C. to 39° C., 15° C. to 39° C., 16° C. to 39° C., 17° C. to 39° C., 18° C. to 39° C., 19° C. to 39° C., 20° C. to 39° C., 21° C. to 39° C., 22° C. to 39° C., 23° C. to 39° C., 24° C. to 39° C., 25° C. to 39° C., 26° C. to 39° C., 27° C. to 39° C., 28° C. to 39° C., 29° C. to 39° C., and 30° C. to 39° C. In a third set of ranges, the temperature is in one of the following ranges: 1° C. to 35° C., 2° C. to 34° C., 3° C. to 33° C., 4° C. to 32° C., 5° C. to 31° C., 6° C. to 30° C., 7° C. to 29° C., 8° C. to 28° C., 9° C. to 27° C., and 10° C. to 26° C.

The period of time during which spores are contacted with a performic-acid containing solution in accordance with the present teachings may be varied based on a desired end use (e.g., the targeted degree of log reduction in the number of spores capable of reproduction, metabolism, and/or growth). In one example, the period of time ranges from about 2 seconds to about 30 seconds. In another example, the period of time ranges from about 3 seconds to about 20 seconds. In a further example, the period of time ranges from about 4 seconds to about 15 seconds. In some embodiments, the period of time is less than or equal to about 15 seconds, less than or equal to about 12 seconds, less than or equal to about 10 seconds, less than or equal to about 7 seconds, or less than or equal to about 5 seconds. Although periods of time outside this range may also be employed (e.g., period of times above about 30 seconds), lower periods of time may minimize costs (e.g., on an automated processing line) and may be preferable for at least this reason.

The period of time during which spores are contacted with a performic-acid containing solution in accordance with the present teachings may be one of several different values or fall within one of several different ranges. For example, it is within the scope of the present teachings to select a period of time to be less than or equal to one of the following values: about 30 seconds, 29 seconds, 28 seconds, 27 seconds, 26 seconds, 25 seconds, 24 seconds, 23 seconds, 22 seconds, 21 seconds, 20 seconds, 19 seconds, 18 seconds, 17 seconds, 16 seconds, 15 seconds, 14 seconds, 13 seconds, 12 seconds, 11 seconds, 10 seconds, 9 seconds, 8 seconds, 7 seconds, 6 seconds, 5 seconds, 4 seconds, 3 seconds, 2 seconds, or 1 second.

It is also within the scope of the present teachings for the period of time during which spores are contacted with a performic-acid containing solution in accordance with the present teachings to fall within one of many different ranges. In a first set of ranges, the period of time is in one of the following ranges: about 1 second to 30 seconds, 2 seconds to 30 seconds, 3 seconds to 30 seconds, 4 seconds to 30 seconds, 5 seconds to 30 seconds, 6 seconds to 30 seconds, 7 seconds to 30 seconds, 8 seconds to 30 seconds, 9 seconds to 30 seconds, and 10 seconds to 30 seconds. In a second set of ranges, the period of time is in one of the following ranges: about 3 seconds to 29 seconds, 3 seconds to 28 seconds, 3 seconds to 27 seconds, 3 seconds to 26 seconds, 3 seconds to 25 seconds, 3 seconds to 24 seconds, 3 seconds to 23 seconds, 3 seconds to 22 seconds, 3 seconds to 21 seconds, 3 seconds to 20 seconds, 3 seconds to 19 seconds, 3 seconds to 18 seconds, 3 seconds to 17 seconds, 3 seconds to 16 seconds, 3 seconds to 15 seconds, 3 seconds to 14 seconds, 3 seconds to 13 seconds, 3 seconds to 12 seconds, 3 seconds to 11 seconds, 3 seconds to 10 seconds, 3 seconds to 9 seconds, 3 seconds to 8 seconds, 3 seconds to 7 seconds, and 3 seconds to 6 seconds. In a third set of ranges, the period of time is in one of the following ranges: about 1 second to 29 seconds, 2 seconds to 25 seconds, 3 seconds to 20 seconds, 4 seconds to 15 seconds, and 5 seconds to 10 seconds.

The degree to which the number of spores capable of reproduction, metabolism, and/or growth may be reduced in accordance with the present teachings is not restricted. In one example, methods in accordance with the present teachings effect at least a 4 log reduction in the number of spores. In another example, methods in accordance with the present teachings effect at least a 5 log reduction in the number of spores. In a further example, methods in accordance with the present teachings effect at least a 6 log reduction in the number of spores. In a further example, methods in accordance with the present teachings effect at least a 7 log reduction in the number of spores. In an additional example, methods in accordance with the present teachings effect at least an 8 log reduction in the number of spores.

The amount of PFA present in an aqueous solution prepared in accordance with the present teachings may be varied based on a desired end use (e.g., the targeted degree of log reduction in the number of spores capable of reproduction, metabolism, and/or growth). In one example, the PFA is present in an amount of at least about 3.25 weight percent relative to total weight of the aqueous solution. In another example, the PFA is present in an amount of at least about 1.0 weight percent relative to total weight of the aqueous solution. In a further example, the PFA is present in an amount of at least about 1.5 weight percent relative to total weight of the aqueous solution. In a further example, the PFA is present in an amount of at least about 2.0 weight percent relative to total weight of the aqueous solution. In a still further example, the PFA is present in an amount of at least about 3.0 weight percent relative to total weight of the aqueous solution. In another example, the PFA is present in an amount of up to about 25 weight percent relative to total weight of the aqueous solution.

The amount of PFA present in an aqueous solution prepared in accordance with the present teachings may be one of several different values or fall within one of several different ranges. For example, it is within the scope of the present teachings to select an amount of PFA to be greater than or equal to one of the following values: about 1.0 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2.0 wt. %, 2.1 wt. %, 2.2 wt. %, 2.3 wt. %, 2.4 wt. %, 2.5 wt. %, 2.6 wt. %, 2.7 wt. %, 2.8 wt. %, 2.9 wt. %, 3.0 wt. %, 3.1 wt. %, 3.2 wt. %, 3.3 wt. %, 3.4 wt. %, 3.5 wt. %, 3.6 wt. %, 3.7 wt. %, 3.8 wt. %, 3.9 wt. %, 4.0 wt. %, 4.1 wt. %, 4.2 wt. %, 4.3 wt. %, 4.4 wt. %, 4.5 wt. %, 4.6 wt. %, 4.7 wt. %, 4.8 wt. %, 4.9 wt. %, 5.0 wt. %, 6.0 wt. %, 7.0 wt. %, 8.0 wt. %, 9.0 wt. %, 10.0 wt. %, 11.0 wt. %, 12.0 wt. %, 13.0 wt. %, 14.0 wt. %, 15.0 wt. %, 16.0 wt. %, 17.0 wt. %, 18.0 wt. %, 19.0 wt. %, 20.0 wt. %, 21.0 wt. %, 22.0 wt. %, 23.0 wt. %, 24.0 wt. %, 25.0 wt. %, 26.0 wt. %, 27.0 wt. %, 28.0 wt. %, 29.0 wt. %, or 30.0 wt. %, by weight of the aqueous solution.

It is also within the scope of the present teachings for the amount of PFA present in an aqueous solution prepared in accordance with the present teachings to fall within one of many different ranges. In a first set of ranges, the amount of PFA is in one of the following ranges: about 1.0 wt. % to 30 wt. %, 1.1 wt. % to 30 wt. %, 1.2 wt. % to 30 wt. %, 1.3 wt. % to 30 wt. %, 1.4 wt. % to 30 wt. %, 1.5 wt. % to 30 wt. %, 1.6 wt. % to 30 wt. %, 1.7 wt. % to 30 wt. %, 1.8 wt. % to 30 wt. %, 1.9 wt. % to 30 wt. %, 2.0 wt. % to 30 wt. %, 2.1 wt. % to 30 wt. %, 2.2 wt. % to 30 wt. %, 2.3 wt. % to 30 wt. %, 2.4 wt. % to 30 wt. %, 2.5 wt. % to 30 wt. %, 2.6 wt. % to 30 wt. %, 2.7 wt. % to 30 wt. %, 2.8 wt. % to 30 wt. %, 2.9 wt. % to 30 wt. %, and 3.0 wt. % to 30 wt. % by weight of the aqueous solution. In a second set of ranges, the amount of PFA is in one of the following ranges: about 2 wt.

% to 29 wt. %, 2 wt. % to 28 wt. %, 2 wt. % to 27 wt. %, 2 wt. % to 26 wt. %, 2 wt. % to 25 wt. %, 2 wt. % to 24 wt. %, 2 wt. % to 23 wt. %, 2 wt. % to 22 wt. %, 2 wt. % to 21 wt. %, 2 wt. % to 20 wt. %, 2 wt. % to 19 wt. %, 2 wt. % to 18 wt. %, 2 wt. % to 17 wt. %, 2 wt. % to 16 wt. %, 2 wt. % to 15 wt. %, 2 wt. % to 14 wt. %, 2 wt. % to 13 wt. %, 2 wt. % to 12 wt. %, 2 wt. % toll wt. %, 2 wt. % to 10 wt. %, 2 wt. % to 9 wt. %, 2 wt. % to 8 wt. %, 2 wt. % to 7 wt. %, 2 wt. % to 6 wt. %, 2 wt. % to 5 wt. %, 2 wt. % to 4 wt. %, and 2 wt. % to 3 wt. % by weight of the aqueous solution. In a third set of ranges, the amount of PFA is in one of the following ranges: about 1.0 wt. % to 29 wt. %, 1.1 wt. % to 28 wt. %, 1.2 wt. % to 27 wt. %, 1.3 wt. % to 26 wt. %, 1.4 wt. % to 25 wt. %, 1.5 wt. % to 24 wt. %, 1.6 wt. % to 23 wt. %, 1.7 wt. % to 22 wt. %, 1.8 wt. % to 21 wt. %, 1.9 wt. % to 20 wt. %, 2.0 wt. % to 19 wt. %, 2.1 wt. % to 18 wt. %, 2.2 wt. % to 17 wt. %, 2.3 wt. % to 16 wt. %, 2.4 wt. % to 15 wt. %, 2.5 wt. % to 14 wt. %, 2.6 wt. % to 13 wt. %, 2.7 wt. % to 12 wt. %, 2.8 wt. % to 11 wt. %, 2.9 wt. % to 10 wt. %, 3.0 wt. % to 9 wt. %, 3.1 wt. % to 8 wt. %, and 3.2 wt. % to 7 wt. % by weight of the aqueous solution.

The type of spores that may be killed in accordance with the present teachings is not restricted. All manner of spores—and combinations thereof—that are perceived as contaminants (e.g., of a surface to be sterilized/disinfected) are contemplated for use. By way of example, spores that may be killed in accordance with the present teachings include but are not limited to bacterial spores, fungal spores, protozoan spores and cysts, spores from seedless plants, and/or the like, and combinations thereof. In some embodiments, the spores include bacterial spores which may include spores from a *Bacillus* and/or *Clostridium* genus. Representative bacterial spores that may be killed in accordance with the present teachings include but are not limited to *Geobacillus stearothermophilus*, *Bacillus atrophaeus*, *Bacillus subtilis*, *Bacillus pumilus*, *Bacillus coagulans*, *Clostridium sporogenes*, *Clostridium botulinum*, *Bacillus subtilis globigii*, *Bacillus cereus*, *Bacillus circulans*, *Bacillus anthracis*, and/or the like, and combinations thereof. In some embodiments, the spores include *Bacillus atrophaeus* ATCC 9372 spores, a relatively resistant bioindicator organism recommended for testing the effects of chemical disinfection or sterilization processes (U.S. Pharmacopeia).

In some embodiments, the PFA-containing aqueous solution is at least-partially aerosolized and, in some embodiments, the methods in accordance with the present teachings further include aerosolizing at least a portion of the aqueous solution (e.g., delivering the aqueous solution to a spore-containing surface via a nebulizer). In some embodiments, methods in accordance with the present teachings include aerosolizing at least a portion of the aqueous solution prior to contacting the spores with the aqueous solution. In some embodiments, the aerosolized form of the PFA-containing aqueous solution contains the dimeric form of PFA shown by formula II above.

While neither desiring to be bound by any particular theory nor intending to limit in any measure the scope of the appended claims or their equivalents, it is presently believed that at least in some embodiments in accordance with the present teachings, the efficacy of PFA in killing spores at relatively high speed and at relatively low temperatures may be enhanced through aerosolization, and that the improved efficacy may arise—at least in part—from the increased surface area provided by aerosolized droplets of the PFA-containing aqueous solution. The conversion of a body of liquid into myriad small-diameter droplets of liquid (e.g., having droplet diameters on the order of about 1 μm, 3.5 μm, and/or 10 μm) results in an orders-of-magnitude increased surface area that is believed to accelerate gas formation.

In addition, while neither desiring to be bound by any particular theory nor intending to limit in any measure the scope of the appended claims or their equivalents, it is also presently believed that the dimeric form of PFA shown in formula II above may be more prone to entering a gaseous state as compared to other peracids since the dimeric form of PFA has less of a tendency to hydrogen bond with water in solution. Whereas other peracids (e.g., RCOOOH in which R is a $C_1$ methyl group or a $C_{>1}$ carbon atom-containing moiety) bind water strongly, the dimeric form of PFA contains its own internal hydrogen bonding as shown by the dashed lines in formula II and is therefore freer to escape from solution. The reduction in hydrogen bonding with water of the dimeric form of PFA leads to an apparent increase in its vapor pressure, which in turn is believed to facilitate its escape from solvation as a gas. The escape of the dimeric form of PFA into the gaseous state may be accelerated by mixing and by increasing the surface area of the solution.

In contrast to the methods in accordance with the present teachings, which may be effective at contact times of less than or equal to about 15 seconds and at temperatures at or near room temperature (e.g., up to about 35° C.), conventional sterilization/disinfection procedures—for examples, ones using hydrogen peroxide and/or peracids (e.g., peracetic acid)—typically require relatively higher temperatures and relatively long times of exposure to achieve on-line sterilization. For example, temperatures greater than about 55° C. to 65° C. and exposure times greater than about fifteen seconds may be employed in conventional techniques.

In some embodiments, the sterilization/disinfection process in accordance with the present teachings involves the application of a liquid and/or gaseous (e.g., aerosolized) fluid mixture via spray, aerosol, stream, fluid flow, bath, gaseous tunnel, and/or the like to one or more surfaces of an article (e.g., packaging) while the article is being conveyed or is in transit on a commercial manufacturing line (e.g., a food or pharmaceutical filling machine, line, system and/or the like). The methods and materials described here may also be used for reducing chemical residuals that might otherwise remain on or in the surfaces subjected to the sterilization/disinfection process.

In accordance with the present teachings, a fluid mixture may be applied to one or more surfaces of articles to be sterilized while they are in a continuous, discontinuous, pulsed, or stop-and-go motion or flow on a filling or manufacturing line. The fluid mixture may be applied as a wet solution or as a vapor. For embodiments in which the fluid mixture is applied as a wet solution, surfaces may be immersed in, sprayed with, or otherwise wetted with a solution containing at least one active compound (e.g., performic acid, hydrogen peroxide, formic acid, peracids, and/or the like). In some embodiments, a fluid mixture (e.g., a mixture of a peroxide, such as hydrogen peroxide, and formic acid; and/or a mixture of hydrogen peroxide and/or a peracid) may be applied by entraining the mixture in a stream of gas, air, heated air, or steam, separately or as a premixed solution, by spraying, metering, injecting, infusing, or otherwise causing the hydrogen peroxide, formic acid, performic acid, peracid, and any other included compounds to be carried on or in a fluid, gaseous, and/or vaporous stream.

Methods in accordance with the present teachings may be used advantageously in on-line processes at high throughput rates in view of the rapidity of the microbial inactivation, disinfection, and/or sterilization that may be achieved, and in further view of the ability to rapidly remove treatment residuals after antimicrobial application. Packaging being conveyed on commercial scale filling systems often travels at high line speeds. In order to inactivate microorganisms that may reside on one or more surfaces of an article to be disinfected or sterilized using conventional methods, relatively long contact times, elevated temperatures, and extended rinsing are oftentimes required. The long contact times between an active agent and a surface to be sterilized/disinfected often dictate that long distances or large areas be devoted to the treatment/sterilization zone, thereby significantly increasing complexity and cost. Moreover, the use of elevated treatment temperatures, either during the application of the active agent or afterwards during rinses or air treatments to reduce residuals, may further add expense and complexity to the system and, in addition, may be problematic in view of the softening and/or damage that may occur with some materials.

In accordance with the present teachings, as demonstrated in the Examples described below, rapid and effective sterilization and/or disinfection and rapid and effective removal and/or reduction of residuals associated with sterilization/disinfection may be achieved through the use of an aqueous solution containing performic acid and/or a mixture containing higher concentrations of peroxide compounds than may be practical in conventional commercial practice (e.g., at least 1.0 weight percent hydrogen peroxide and, in some cases, more than 50 weight percent hydrogen peroxide).

In accordance with the present teachings, methods are provided for the rapid elimination of peroxide oxidative residuals and the enhancement of sterilization/disinfection. For example, in some embodiments, methods in accordance with the present teachings further include treating a surface that has been treated with with an aqueous solution in accordance with the present teachings with a rinse solution that contains one or more active chemistries configured to react with one or more residual oxidative species (e.g., peroxides) to reduce oxidative capacity thereof. In some embodiments, the rinse solution containing the one or more active chemistries is applied at a temperature of less than about 60° C.

As described above, a fluid mixture in accordance with the present teachings may be applied as a wet solution or as a vapor. For embodiments in which the fluid mixture is applied as a wet solution, removal of residuals may be achieved using hot, sterile air, a pH change, and/or a Fenton reaction chemistry, as further described below. If the fluid mixture is nebulized prior to application and is applied as a gas, residuals may be removed with a burst of sterile air or by pulling a quick vacuum (e.g., on a sterilized package).

In some embodiments, the active chemistry used to reduce peroxide oxidative capacity involves rapidly shifting to alkaline pH values through the use of an alkaline agent (e.g., an alkaline salt, such as sodium hydroxide) to enhance and accelerate the effects of sterilization/disinfection mixtures containing peroxides. The peroxides undergo destabilization, and their decomposition and the attendant formation of hydroxyl radicals is accelerated. The use of alkaline agents to react with peroxides is described in the following United States patent documents: U.S. Patent Application Publication No. 2007/0006551; U.S. Patent Application Publication No. 2008/023325; and U.S. Pat. No. 7,481,974. Each of these three documents is hereby incorporated by reference in its entirety, except that in the event of any inconsistent teachings or definition from the present specification, the teachings or definition herein shall be deemed to prevail.

In some embodiments, the active chemistry used to reduce peroxide oxidative capacity involves using a metal (e.g., a transition metal) to achieve peroxide bond destabilization. Transition metals may participate in a Fenton reaction with peroxide to provide an alternative method for the rapid reduction of peroxide oxidative capacity and removal of peroxide residues. In the Fenton Reaction, as originally described in the nineteenth century, ferrous iron (II) is oxidized by hydrogen peroxide to ferric iron(III), a hydroxyl radical, and a hydroxyl anion, as shown in EQN. (2). Iron(III) is then reduced back to iron(II), a peroxide radical, and a proton by the same hydrogen peroxide (disproportionation), as shown in EQN. (3). In the appropriate pH range, the net reaction is truly catalytic and two molecules of hydrogen peroxide are converted into two hydroxyl radicals and water. The Fe(II) is regenerated by secondary reactions with peroxide.

$$Fe2++H2O2 \rightarrow Fe3++OH.+OH- \qquad \text{EQN. (2)}$$

$$Fe3++H2O2 \rightarrow Fe2++OOH.+H+ \qquad \text{EQN. (3)}$$

Following the early work by Fenton, it has been demonstrated that many transition metal ions besides iron (including, for example, copper, gold, chromium, cobalt, cerium, mercury, manganese, vanadium, cadmium, zinc, nickel, tin, cadmium, and others) are capable of valence state transitions that may also participate in the catalytic decomposition of peroxides. Therefore, many different transition metal ions may be used in accordance with the present teachings to reduce peroxide residuals. However, in some embodiments, iron is used because of its nutritional safety and benefits.

In accordance with the present teachings, a rinse solution containing an active chemistry of a type described above (e.g., chemical agents to produce a rapid shift in pH, thereby accelerating the decomposition of peroxide residues and/or the employment of Fenton reaction chemistries to accelerate the decomposition of peroxides) may be used for the rapid elimination of peroxide residues remaining on or in a material, package, or container. Additional methods and chemistries also exist that may be used efficaciously for the rapid removal of peroxide residues. For example, these additional methods include but are not limited to the use of pyruvate salts (e.g., sodium pyruvate and/or the like), ascorbate salts (e.g., sodium ascorbate and/or the like), enzymatic methods (e.g., catalase and/or the like), bisulfite salts (e.g., sodium bisulfite and/or the like), sulphite salts (e.g., sodium sulphite and/or the like), thiosulfite salts (e.g., sodium thiosulfite and/or the like), thiosulfate salts (e.g., sodium thiosulfate and/or the like), activated carbon, clay (e.g., bentonite, montmorillonite, and/or the like), pH-adjustment agents, elevated temperatures, and/or the like, and combinations thereof.

In some embodiments, the rinse solution contains a chemical reagent such as an alkaline salt for shifting pH (e.g., NaOH), a transition metal ion (e.g., Fe), an enzyme (e.g., catalase), and/or the like.

In some embodiments, methods in accordance with the present teachings use a peroxide-based mixture for sterilization/disinfection and then employ methods for the rapid removal of peroxide oxidative residuals that might otherwise serve as accelerants of peroxide-based sterilization/disinfection. The methods for rapid reduction of peroxide residual levels may, in some embodiments, facilitate the use of higher concentrations of peroxide in sterilization/disinfection mixtures than would normally be considered since the use of such higher concentrations of peroxide may be limited based on conventional considerations of peroxide residual attenuation or removal.

Methods in accordance with the present teachings for the rapid sterilization/disinfection of surfaces may include the rapid reduction of oxidative peroxide residuals from the surface using peroxide-based mixtures for sterilization/disinfection, and then rapid removal of peroxide oxidative residuals employing methods that might else-wise serve as accelerants of peroxide-based sterilization/disinfection.

Methods in accordance with the present teachings for the rapid sterilization/disinfection of surfaces may use peroxide-based mixtures for sterilization/disinfection and may be conducted at relatively low temperatures of less than about 60° C.

Methods in accordance with the present teachings for the rapid sterilization/disinfection of surfaces may use peroxide-based mixtures for sterilization/disinfection and relatively low contact times with the sterilization/disinfection mixture of less than about 12 seconds.

Methods in accordance with the present teachings for the rapid sterilization/disinfection of surfaces may use peroxide-based mixtures for sterilization/disinfection in which the peroxide mixture includes formic acid (methanoic acid) or performic acid (permethanoic acid), either of which may be used at a concentration greater than or equal to about 1 wt. % at a temperature of less than about 60° C. and for a contact time before rinsing of less than about 12 seconds.

Methods for the rapid sterilization/disinfection of surfaces may use peroxide-based mixtures for sterilization/disinfection in which the peroxide mixture includes peracetic acid (ethanoic acid) or peracetic acid (perethanoic acid), or propionoic acid (propanoic acid) or propionoic peracid (propanoic peracid), or a mixture of these with or without the addition of formic acid, any of or the combination of which may be used at a concentration greater than or equal to about 1 wt. % at a temperature of less than about 60° C. and for a contact time before rinsing of less than about 12 seconds.

The following examples and representative procedures illustrate features in accordance with the present teachings, and are provided solely by way of illustration. They are not intended to limit the scope of the appended claims or their equivalents.

EXAMPLES

General

All reagents are commercially available and were used without further purification unless otherwise noted. Hydrogen peroxide (ACS reagent grade, 30 wt. % in $H_2O$, contains inhibitor) and formic acid (reagent grade, ≥95 wt. % in $H_2O$) were purchased from Sigma-Aldrich (St. Louis, Mo.). Hydrogen peroxide (UP-HTP grade, 50 wt. % in $H_2O$) was purchased from FMC Corporation (Philadelphia, Pa.). Formic acid (95 wt. % in $H_2O$) was purchased from DudaDiesel (Decatur, Ala.). Catalase from *Aspergillus niger* was purchased from MP Biomedicals (Santa Ana, Calif.).

An aqueous solution containing x weight percent of performic acid may be prepared by (1) diluting a commercially available aqueous solution of hydrogen peroxide (e.g., a 30 weight percent aqueous solution or a 50 weight percent aqueous solution) down to a concentration of 2x; (2) diluting a commercially available aqueous solution of formic acid (e.g., a 95 weight percent aqueous solution) down to a concentration of 2x; and (3) combining the diluted solution of hydrogen peroxide and the diluted solution of formic acid in a 1:1 volume, thereby providing performic acid in a concentration of x.

The procedure for performing spore inactivation tests in solution is as follows: *Bacillus atrophaeus* ATCC 9372 spores in saline were equilibrated in a water bath at the preselected test temperature, as was a formic acid/hydrogen peroxide mixture. At an initial time ($T_0$), a volume of the formic acid/peroxide mixture was added to the spore preparation, such that the pre-chosen test concentration of the sterilization agent was achieved. At preselected times after the addition of the sterilization agent to the spore preparation, aliquots of the spore-treated mixture were transferred into a solution containing an excess of catalase (MP Biomedical) in order to quench the peroxide reaction. This solution was then serially ten-fold diluted and spread-plated onto tryptic soy agar plates that were subsequently incubated at 35° C. for 48 hours and enumerated.

Example 1

A commercial preparation of *Bacillus atrophaeus* ATCC 9372 spores characterized in its response to both ethylene oxide and hydrogen peroxide was selected for use in this experiment because of the known high relative resistance to dry heat or chemical inactivation of these spores. The spores of *Bacillus atrophaeus* American Type Culture Collection (ATCC) 9372 (formerly known as *Bacillus subtilis* variety *niger*, strain *globigii*) are recommended in the U.S. Pharmacopeia as the bioindicator for processes using dry heat, hydrogen peroxide, or chemicals as the active agent. The experimentally determined response of the *Bacillus atrophaeus* ATCC 9372 spore preparation to treatment with 28% hydrogen peroxide at various temperatures is shown in FIG. 1.

The experimental data shown in FIG. 1 were obtained by direct injection of a one-twentieth volume of spores into a volume of a hydrogen peroxide solution (final concentration equals 28%) solution pre-equilibrated at the temperature referenced. At the times noted, a 0.1-milliliter aliquot was withdrawn and the peroxide activity rapidly quenched by injection of the aliquot into a nine-fold volume of a room temperature solution containing excess catalase (from *Aspergillus niger*). The mixture was then serially ten-fold diluted in saline and spread-plated on tryptic soy agar.

The z-value shown as an insert on the plot in FIG. 1 was extrapolated (chart not shown) by plotting the logarithm of the experimentally-determined D-values from FIG. 1. The data in FIG. 1 show that this spore preparation possesses relatively high resistance to hydrogen peroxide and a resistance typical of that possessed by spore preparations used in tests to measure the effectiveness and efficacy of sterilization machines and systems using hydrogen peroxide.

Example 2

The experimental data shown in Table 1 were obtained by direct injection of a 10-microliter volume of the spore preparation, shown in FIG. 1 and characterized as to its hydrogen peroxide response, into 0.5 milliliter of a pre-equilibrated formic acid, hydrogen peroxide, water mixture. The abbreviation CFU in Table 1 refers to "colony forming units."

The two concentrations of the formic acid, hydrogen peroxide, water mixture used were a stock solution and one-to-five dilution of the stock solution. At the time noted, a 0.1-milliliter aliquot was withdrawn and the peroxide activity rapidly quenched by injection of this aliquot into a nine-fold volume of a room temperature, 1 M, pH 7.2 phosphate buffer solution containing excess catalase (from *Aspergillus niger*). The mixture was then serially ten-fold diluted in saline, spread-plated on tryptic soy agar, and incubated at 35° C.

TABLE 1

Inactivation data of *Bacillus atrophaeus* ATCC 9372 spores produced by 5 or 10 seconds of exposure at 65° C.

| Agent Concentration | Temperature (° C.) | Time (seconds) | Spore Recovery |
|---|---|---|---|
| ⅕ Dilution | 65 | 5 | 0 CFU |
| ⅕ Dilution | 65 | 10 | 0 CFU |
| Full Strength | 65 | 5 | 0 CFU |
| Full Strength | 65 | 10 | 0 CFU |
| Control (Untreated) | 65 | 10 | 7.2 Log CFU |

As shown in Table 1, greater than 7 logs of inactivation were obtained. The results suggest that at this temperature, the sterilization/disinfection mixture used provides a significant enhancement of inactivation effects as compared to hydrogen peroxide. In FIG. 1, treatment with 28% hydrogen peroxide at 65° C. produces approximately one logarithm of spore inactivation per every seven seconds of contact time at 65° C. By contrast, as shown in Table 1, more than 7 logarithm cycles of inactivation are produced during both 5 and 10 seconds of contact at 65° C.

Example 3

Table 2 shows the results obtained from treating the *Bacillus atrophaeus* ATCC 9372 spore preparation at a range of temperatures and contact times. The results shown were obtained using two different concentrations of the sterilization/disinfection mixture: one mixture was termed full strength and the other mixture was its one-to-five dilution in saline.

TABLE 2

Inactivation data of *Bacillus atrophaeus* ATCC 9372 spores produced by various contact times at various temperatures.

| Agent Concentration | Temperature (° C.) | Time (seconds) | Spore Recovery |
|---|---|---|---|
| ⅕ Dilution | 60 | 15 | 0 CFU |
| ⅕ Dilution | 60 | 60 | 0 CFU |
| ⅕ Dilution | 45 | 15 | 0 CFU |
| ⅕ Dilution | 45 | 60 | 0 CFU |
| Control, Untreated | 60 | 60 | 7.7 Log CFU |
| Full Strength | 50 | 15 | 0 CFU |
| Full Strength | 50 | 60 | 0 CFU |
| Control, Untreated | 50 | 60 | 6.4 Log CFU |
| Full Strength | 50 | 15 | 0 CFU |
| Control, Untreated | 50 | 15 | 7.5 Log CFU |
| ⅕ Dilution | 30 | 15 | 6.5 Log CFU |
| Full Strength | 30 | 15 | 0 CFU |
| Full Strength | 30 | 60 | 0 CFU |
| Full Strength | 30 | 120 | 0 CFU |
| Control, Untreated | 30 | 120 | 6.8 Log CFU |
| Full Strength | 30 | 5 | 0 CFU |
| Full Strength | 30 | 10 | 0 CFU |
| Control, Untreated | 30 | 10 | 6.9 Log CFU |

The results illustrated in Table 2 show that the sterilization/disinfection mixture is effective for producing high levels of *Bacillus atrophaeus* ATCC 9372 spore inactivation across a wide range of temperatures and contact times. Moreover, it is shown that the full strength configuration of the sterilization/disinfection mixture is effective even using a very short contact time (5 seconds) at relatively low temperature (30° C.).

The results shown in Table 2 are grouped as performed along with the attendant untreated control sample results indicating the original spore inoculation level for each series of experiments.

Example 4

An aqueous solution containing 3.25 wt. % of performic acid was prepared by (1) diluting a 50 wt. % aqueous solution of hydrogen peroxide down to a concentration of 6.5 wt. %; (2) diluting a 95 wt. % aqueous solution of formic acid down to a concentration of 6.5 wt. %; and (3) combining the 6.5 wt. % solution of hydrogen peroxide and the 6.5 wt. % solution of formic acid in a 1:1 volume.

The experimentally determined response of the *Bacillus atrophaeus* ATCC 9372 spore preparation to treatment with 3.25 wt. % performic acid at various temperatures and for various durations of time is summarized in Table 3.

TABLE 3

Inactivation data of *Bacillus atrophaeus* ATCC 9372 spores produced by 3.25 wt. % performic acid at various times and temperatures.

| Treatment Conditions | Colony Forming Units (CFU) | Log | Log Reduction |
|---|---|---|---|
| 10° C. (control) | 70000000 | 7.8451 | |
| 20° C. (control) | 91000000 | 7.959 | |
| Average (control) | 0 | 7.9058 | |
| 10° C., 5 seconds | 0 | | >7.8 |
| 10° C., 10 seconds | 0 | | >7.8 |
| 10° C., 15 seconds | 0 | | >7.8 |
| 20° C., 5 seconds | 0 | | >8 |
| 20° C., 10 seconds | 0 | | >8 |
| 20° C., 15 seconds | 0 | | >8 |

Thus, as shown by the data in Table 3, performic acid is surprisingly and unexpectedly effective in killing *Bacillus atrophaeus* ATCC 9372 spores at room temperature and below (e.g., 5° C. or 10° C.) after exposure times as little as 5 seconds. To place this surprising and unexpected efficacy in context, the significantly less efficacious usage regimes of hydrogen peroxide and peracetic acid are contrasted with that of PFA in Table 4.

TABLE 4

Efficacy usage regimes of hydrogen peroxide and peracetic acid as compared to performic acid.

| Treatment Conditions | Temperature (° C.) | Time (seconds) |
|---|---|---|
| Hydrogen Peroxide | 65 | 15-30 |
| Peracetic Acid | 55 | 15 |
| Performic Acid | Room Temperature | 5 |

The foregoing detailed description and the accompanying drawing FIGURE have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A method for killing spores comprising:
contacting the spores with an aqueous solution comprising performic acid, wherein the performic acid is present in an amount of between about 1.0 weight percent and about 30 weight percent relative to total weight of the aqueous solution, wherein the contacting occurs at a temperature of between about 5° C. and about 35° C. for a period of time of between about 4 seconds and about 15 seconds, wherein the contacting effects at least a 4 log reduction in a number of spores capable of reproduction, metabolism, and/or growth, and wherein the method does not require activation by heat or ultraviolet light.

2. The process of claim 1 wherein the temperature is less than or equal to about 30° C. and the period of time is less than or equal to about 12 seconds.

3. The method of claim 1 wherein the temperature is less than or equal to about 27° C. and the period of time is less than or equal to about 10 seconds.

4. The method of claim 1 wherein the period of time is less than or equal to about 7 seconds.

5. The method of claim 1 wherein the period of time is less than or equal to about 5 seconds.

6. The method of claim 1 wherein the contacting effects at least a 5 log reduction in the number of spores capable of reproduction, metabolism, and/or growth.

7. The method of claim 1 wherein the contacting effects at least a 6 log reduction in the number of spores capable of reproduction, metabolism, and/or growth.

8. The method of claim 1 wherein the contacting effects at least a 7 log reduction in the number of spores capable of reproduction, metabolism, and/or growth.

9. The method of claim 1 wherein the aqueous solution is at least partially aerosolized.

10. The method of claim 1 further comprising aerosolizing at least a portion of the aqueous solution.

11. The method of claim 1 wherein the aqueous solution is aerosolized prior to the contacting.

12. The method of claim 1 further comprising generating the performic acid from a reaction between a peroxide and formic acid.

13. The method of claim 1 wherein the aqueous solution further comprises formic acid, hydrogen peroxide, or a combination thereof.

14. The method of claim 1 wherein the aqueous solution further comprises distilled water, deionized water, osmosis-purified water, tap water, or a combination thereof.

15. The method of claim 1 wherein the performic acid is present in an amount of at least about 1.5 weight percent based on total weight of the aqueous solution.

16. The method of claim 1 wherein the performic acid is present in an amount of at least about 2 weight percent based on total weight of the aqueous solution.

17. The method of claim 1 wherein the performic acid is present in an amount of at least about 3 weight percent based on total weight of the aqueous solution.

18. The method of claim 1 wherein the spores comprise bacterial spores.

19. The method of claim 1 wherein the spores comprise bacterial spores of a genus selected from the group consisting of *Bacillus, Clostridium*, and a combination thereof.

20. The method of claim 1 wherein the spores comprise bacterial spores selected from the group consisting of *Geobacillus stearothermophilus, Bacillus atrophaeus, Bacillus subtilis, Bacillus pumilus, Bacillus coagulans, Clostridium sporogenes, Clostridium botulinum, Bacillus subtilis globigii, Bacillus cereus, Bacillus circulans, Bacillus anthracis*, and combinations thereof.

21. The method of claim 1 wherein the spores comprise *Bacillus atrophaeus* ATCC 9372 spores.

22. The method of claim 1 wherein the performic acid comprises an intramolecularly hydrogen-bonded monomeric form thereof.

23. The method of claim 1 wherein at least a portion of the spores are present on a surface.

24. The method of claim 1 wherein at least a portion of the spores are present on a surface of an article to be sterilized in an automated processing line.

25. The method of claim 1 wherein at least a portion of the spores are present on a surface, and wherein the method further comprises reducing residual oxidative activity at the surface.

26. The method of claim 25 wherein the reducing comprises treating the surface with a rinse solution comprising a chemical reagent configured to react with one or a plurality of residual oxidative species.

27. The method of claim 26 wherein the chemical reagent comprises an alkaline salt for shifting pH, an ionic metal, a pyruvate salt, an ascorbate salt, an enzyme, a bisulfite salt, a sulphite salt, a thiosulfate salt, activated carbon, clay, or a combination thereof.

28. The method of claim 26 wherein the chemical reagent comprises sodium hydroxide, catalyse, an iron salt, or a combination thereof.

29. A method for killing spores comprising:
contacting the spores with an aqueous solution comprising performic acid, wherein the performic acid is present in an amount of between about 1.0 weight percent and about 30 weight percent relative to a total weight of the aqueous solution, wherein the contacting occurs at a temperature of between about 5° C. and about 30° C. for a period of time of between about 4 seconds and about 10 seconds, wherein the contacting effects at least a 6 log reduction in a number of spores capable of reproduction, metabolism, and/or growth, and wherein the method does not require activation by heat or ultraviolet light.

30. The method of claim 29 further comprising aerosolizing at least a portion of the aqueous solution prior to the contacting.

31. The method of claim 29 further comprising generating the performic acid from a reaction between hydrogen peroxide and formic acid.

32. The method of claim 29 wherein the performic acid is present in an amount of at least about 1.5 weight percent based on total weight of the aqueous solution.

33. A method for killing spores comprising:
contacting the spores with an aqueous solution comprising performic acid, and/or a mixture of formic acid and hydrogen peroxide, in an amount of between about 1.0 weight percent and about 30 weight percent based on total weight of the aqueous solution, wherein at least a portion of the aqueous solution is in fluid communication with an aerosolized form thereof, wherein the contacting occurs at a temperature of between about 5° C. and about 30° C. for a period of time of between about 4 seconds and about 10 seconds, wherein the contacting effects at least a 6 log reduction in a number of spores capable of reproduction, metabolism, and/or growth, and wherein the method does not require activation by heat or ultraviolet light.

34. The method of claim 33 wherein the period of time is less than or equal to about 7 seconds.

* * * * *